US008408080B2

(12) United States Patent
Damikolas

(10) Patent No.: US 8,408,080 B2

(45) Date of Patent: Apr. 2, 2013

(54) APPARATUS FOR RAPIDLY VERIFYING TOLERANCES OF PRECISION COMPONENTS

(75) Inventor: Gerry Damikolas, Upland, CA (US)

(73) Assignee: Kwikset Corporation, Foothill Ranch, CA (US)

( * ) Notice: Subject to any disclaimer, the term of this patent is extended or adjusted under 35 U.S.C. 154(b) by 359 days.

(21) Appl. No.: 12/768,402

(22) Filed: Apr. 27, 2010

(65) Prior Publication Data

US 2010/0269602 A1 Oct. 28, 2010

Related U.S. Application Data

(60) Provisional application No. 61/214,711, filed on Apr. 27, 2009.

(51) Int. Cl.
*G01N 33/00* (2006.01)

(52) U.S. Cl. ........................................................ 73/865.8

(58) Field of Classification Search ................. 209/44.2, 209/644, 932, 586, 939; 73/865.8
See application file for complete search history.

(56) References Cited

U.S. PATENT DOCUMENTS 7,658,291 B2 * 2/2010 Valerio ........................ 209/559

* cited by examiner

*Primary Examiner* — Peter Macchiarolo
*Assistant Examiner* — Tamiko Bellamy
(74) *Attorney, Agent, or Firm* — Barnes & Thornburg LLP

(57) ABSTRACT

An automated inspection system for inspecting, sorting and re-coining each of the locking bar, the rack, and the pin of a rekeyable lock cylinder, as well as other small close-tolerance components in an average cycle time of 1.5 seconds. The inspection system includes a high-speed pneumatic sorting matrix which selectively transfers the components into various length measuring stations, camera inspection stations, mechanical gauge stations, and/or coining stations, and then positions the parts at those stations for combined gauge and visual tolerance checking and sorting. Defects are identified by a combination of visual and machine-gauge inspection, and the sorted components are sorted into three bins: rejects; good parts; and parts for coining. The inspection/sorting system is capable of tolerance-checking down to 0.00011811", with a repeatability of 0.00005906.

15 Claims, 11 Drawing Sheets

A

B

APPARATUS FOR RAPIDLY VERIFYING TOLERANCES OF PRECISION COMPONENTS

CROSS-REFERENCE TO RELATED APPLICATIONS

The present application derives priority from U.S. provisional application Ser. No. 61/214,711 filed 27 Apr. 2009.

FIELD OF THE INVENTION

The present invention relates to inspection machines for small precision parts, and more particularly, to an optical and mechanical inspection station capable of high speed sorting and high-tolerance checking down to 0.0001" (controlling thickness to very tight tolerances), and coining to perfect deformed, bent or oversize parts.

SUMMARY OF THE INVENTION

The present invention is an automated system comprising an adaptable combination of optical inspection stations and precision mechanical gauge stations for high-speed small-tolerance inspection, and a coining station to repair bent, deformed or oversize (excessively thick) parts. An additional mechanical gauge station verifies that the parts were repaired according to the specified tolerances. The system architecture is adaptable to inspecting and repairing any precision metal parts with small or polished surface features, and is particularly well-suited for inspecting and repairing the locking bar and rack of a rekeyable lock cylinder, and for inspecting and sorting the welded pins therein. The present inspection stations allow parts tolerance verification of these extremely small parts in a cycle time between 0.7 to 2.3 seconds, which can potentially raise production with higher yields from 110M parts/year (by 100% manual inspection) to 275M parts/year by automated inspection and part "coining" (repairing).

Coining is a known method of precision stamping in which a workpiece is subjected to a sufficiently high stress to induce plastic flow on the surface of the material. Coining is used to manufacture parts for all industries, and when referred to herein connotes reforming existing parts with high relief or very fine features to correct imperfections. Thus, the present system is a high-volume inspection system for small precision parts capable of both detecting and correcting imperfections.

The present system may incorporating various combinations of visual inspection station(s), mechanical inspection station(s), and a coining station, as appropriate for the production parts. The stations are modular, and there may be different production scenarios for each of the racks, pins and locking bars, depending on demand. The speed of the system is achieved by a novel ultra-high-speed pneumatic sorting/positioning matrix that reorients the components into the various camera-inspection and mechanical-gauge-inspection stations for combined gauge and visual tolerance checking.

By way of background FIG. 1 illustrates a typical rekeyable lock cylinder, which comprises a plug assembly 14, a lock cylinder body 12, and a retainer clip 16. The plug assembly 14 includes a plurality of spring-loaded pins 113. The plug assembly 14 includes a keyway opening 52, a rekeying tool opening 54 and a pair of channels 56 extending radially outwardly for receiving anti-drilling ball bearings 60. The carrier sub-assembly 42 includes a carrier 90, a plurality of racks 92, a spring-loaded locking bar 94 journaled into the carrier 90 and biased by springs 95, and a return spring 98. The carrier sub-assembly 42 and the plug body 14 combine to form a cylinder that fits inside the lock cylinder body 12.

To rekey the lock cylinder 10, a valid key is inserted into the keyway 52 and is rotated approximately 90 degrees counterclockwise or clockwise from the home position. A learning tool or other pointed device is inserted into the rekeying tool opening 54 and is pushed against the carrier 90 to move the carrier 90 parallel to the longitudinal axis of the lock cylinder 10 into a learn mode. The valid key is removed and a second valid key is inserted and rotated clockwise or counterclockwise. The carrier 90 is biased toward the plug assembly 14 face by the return spring 98, causing the racks 92 to re-engage the pins 113. The racks 92 each include a frontal pin-engaging surface having a plurality of gear teeth configured to engage the annular gear teeth of the pins 113, a semi-circular recess at the bottom, and a backside surface with a plurality of anti-pick grooves and a pair of locking bar-engaging grooves. The plurality of spring-loaded pins 113 are generally cylindrical with annular gear teeth and a central longitudinal bore for receiving biasing springs 115. The spring-loaded locking bar 94 is configured to fit into a recess in the carrier 90 and also includes triangular edges configured to fit into grooves.

The racks 92, pins 113 and locking bar 94, are small extreme precision parts that must be manufactured to very tight tolerances. In a production environment this necessarily entails a thorough 100% inspection and, where necessary, coining for compliance before use in the field. It should be apparent from FIG. 1 that a thorough 100% inspection for compliance is a time-consuming task in a production environment. Indeed, conventional inspection methods are predominantly manual. Each discrete part must be placed in an optical inspection station and visually inspected under magnification with reference to a measurement gauge or must be measured by mechanical gauges depending on the geometry and part size. This tedious process limits mass production to approximately 30M parts/year.

What is needed is an automated or semi-automated inspection process that can raise production and quality levels drastically, via a system with automated optical and mechanical inspection stations using a configuration that is adaptable to inspecting the locking bar, the rack, and the pin, and for automated coining (resizing) and sorting of bent or oversize racks and locking bars that exceed drawing specifications to meet tight tolerances.

It is also desirable that the inspection system be modular. A thorough inspection involves a combination of visual inspections and mechanical gauge inspections, optionally followed by coining of components that failed an inspection. The racks 92, pins 113 and locking bar 94 differ, and production requirements may vary. It follows that the particular combination and sequence of inspections and coining may vary. Consequently, for each component part there may be several suitable system configurations available to satisfy the various inspection and/or coining needs.

SUMMARY OF THE INVENTION

The present system accomplishes the foregoing for the components of rekeyable lock cylinders including racks, pins and locking bars, as well as any other small high-precision parts that must be manufactured to very tight tolerances. The system is modular and easily reconfigurable to accommodate possible variations in system configuration and operation. Despite the desired number or sequence of inspections, it remains necessary to sort, convey and orient the components through and into each of the plurality of inspection/coining stations. This high-speed sorting, conveying and orientation is herein achieved with an ultra-high-speed pneumatic sorting/positioning matrix that reorients the components into the various camera inspection and gauge stations for combined gauge and visual tolerance checking. Defects are identified by a combination of visual and machine-gauge inspection, and the components are sorted into three bins: 1) rejects; 2) good parts; 3) parts for coining. The sorters orient and feed the components to a dispenser that dispenses the sorted components single file from a queue.

Rather than merely sorting components for coining, the system can also be configured with an integral coining station for resizing the parts, followed by a mechanical thickness gauge for checking the coining result. The automated optical and mechanical gauge inspection station(s), component sorters and component dispensers, and coining station are adaptable to the various machine configurations shown above for each of the locking bar, rack, and pin components, and will herein be described in the context of a Locking Bar System Configuration including a visual inspection station and mechanical gauge for thickness and straightness sorting of the locking bar in the X-Direction, a component sorter for 90° part rotation, and then another visual inspection station and mechanical gauge for thickness and straightness sorting in the Y-Direction.

For each component part there may be several suitable system configurations available to satisfy the various inspection and/or coining needs. For example, the following configurations of the present system are suitable for the various components as follows:

1. Rack System Configurations (3 Examples)
 a. Visual Inspection Station plus Mechanical Gauge for thickness and straightness inspection and sorting;
 b. Mechanical Gauge with Coining Station for resizing parts, and another Mechanical Gauge to sort resized parts;
 c. Visual Inspection Station with Mechanical Gauge and Coining Station for resizing parts and another Mechanical Gauge to sort resized parts
2. Pin System Configurations (Two Examples)
 a. Feeder Bowl to separate unwanted welded pins (Caused by metal injection molding ("MIM") Sintering Process) from single pins;
 b. Welded Pin Separator and Visual Inspection Station
3. Locking Bar System Configurations (Three Examples)
 a. Visual Inspection Station with Mechanical Gauge for thickness and straightness sorting in the X plane, 90° Part Rotator and Visual Inspection Station with Mechanical Gauge for thickness and straightens sorting in the Y plane;
 b. Mechanical Gauge with Coining for Resizing Parts, followed by Mechanical Gauge to sort resized parts;
 c. Visual Inspection Station with Mechanical Gauge and Coining for resizing parts, followed by Mechanical Gauge to sort resized parts.

In each of the foregoing system configurations it is possible to electronically enable or disable all or some of the stations. For example, for the Locking Bar System Configuration (a), it is possible to turn OFF the visual inspection station and leave ON the Mechanical Gauge, or vice versa.

The system as a whole is capable of tolerance-checking down to 0.00011811", with a repeatability of 0.00005906.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Figure 1:
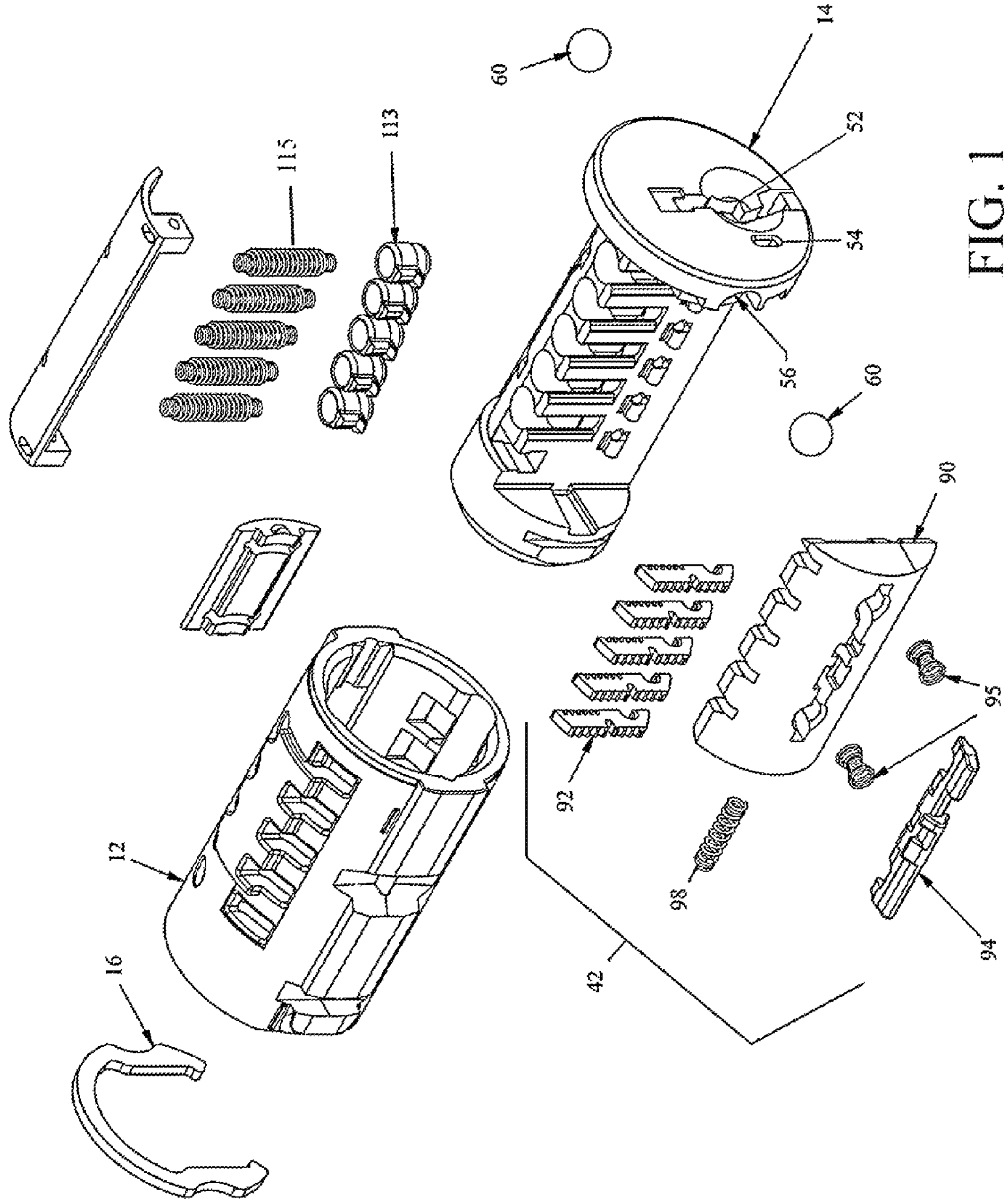
FIG. 1 illustrates a typical rekeyable lock cylinder, with various close-tolerance components.

The present invention is an automated optical and mechanical inspection, sorting and coining system capable of high speed sorting and small-tolerance checking down to 0.0001", plus coining and re-inspection to straighten bent or oversized parts. The optical/mechanical inspection and coining system employs an adaptable multi-station architecture suitable for both optical and mechanical inspection, as well as coining and re-inspection, specifically adapted for each of the locking bar, rack, and pin of a rekeyable lock cylinder, and other small parts. Rekeyable lock cylinder components are shown, for example, in U.S. Pat. No. 6,862,909 to Armstrong et al. and FIG. 1 which is reproduced herein. Again, FIG. 1 illustrates a rekeyable lock cylinder with racks 92, pins 113 and locking bar 94, all of which require optical and mechanical inspection, sorting and coining as facilitated by the present system.

The present system includes a configurable series of optical and mechanical inspection stations, plus sorting and coining stations, that allow parts tolerance verification of extremely small parts in an average cycle time of 1.5 seconds (2.3 seconds (max)), and is capable of tolerance-checking down to 0.00011811", with a repeatability of 0.00005906".

The system cycle time is variable from 0.7 to 2.3 seconds subject to the number of sorting stations needed for optical inspection, mechanical gauging and coining, and desired component yields.

Figure 2:
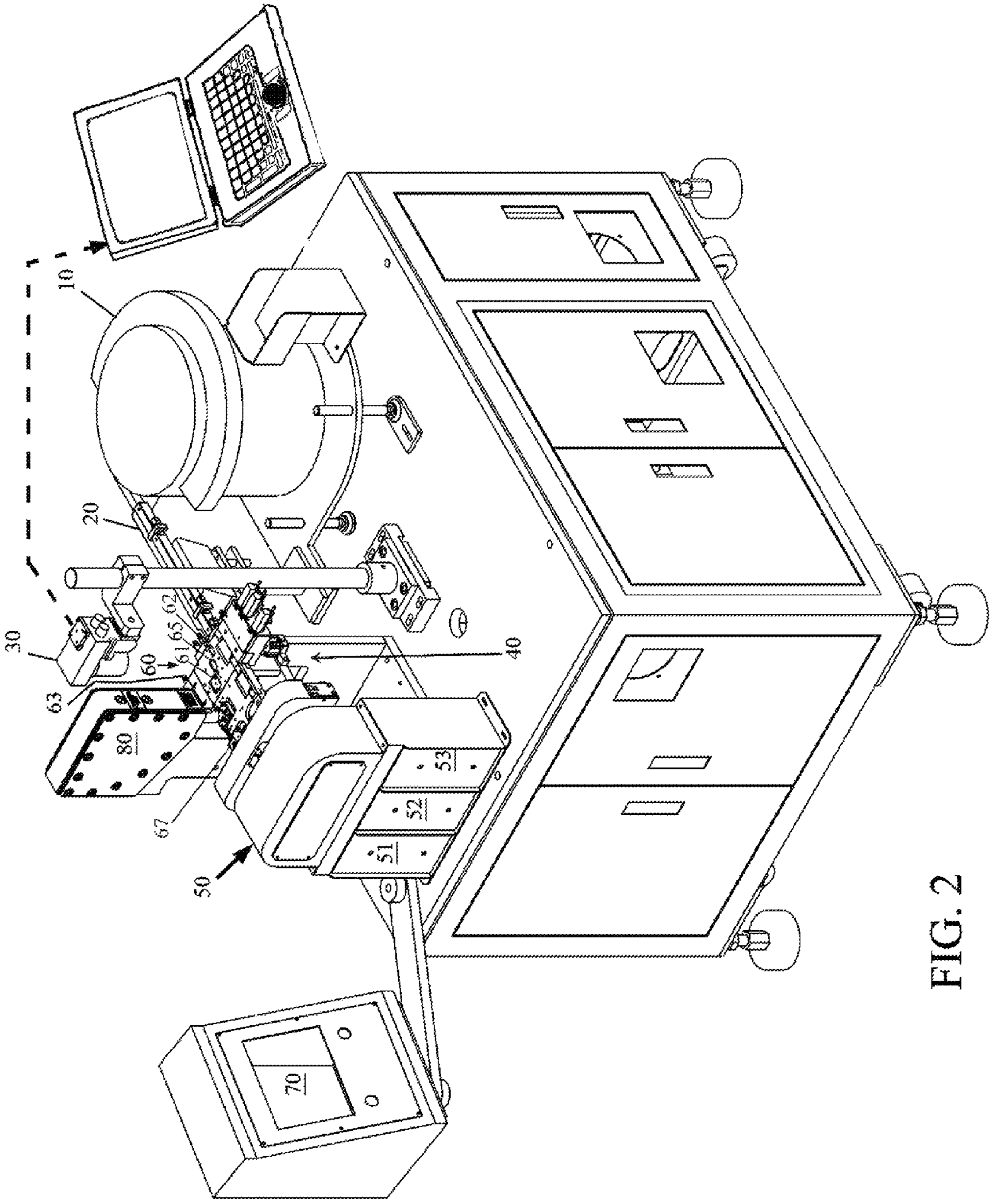
FIG. 2 is a perspective view of an automated machine with one optical inspection station, a part rotator and two mechanical thickness gauges, adapted for inspecting the locking bar according to an embodiment of the present invention.

FIG. 2 is a perspective view of an automated inspection system for inspecting, coining and sorting according to an exemplary embodiment of the present invention. The illustrated inspection system generally includes a vibrating feeder bowl 10 for vibratory feeding of locking bars to an inline single-file conveyor 20. The conveyor 20 transfers the individual locking bars and infeeds them in an indexed manner one-by-one into a sorting assembly 40.

The vibrating feeder bowl 10 accepts bulk components onto a vibrating bowl which aligns them against a circular sidewall. The components line-up against the sidewall where they are fed in a continuous stream onto the inline single-file feed vibratory conveyor 20 (arranged as a linear track). The vibrating feeder bowl 10 is continuous motion with adjustable vibration frequency and feed rate. A variety of vibratory feeders are commercially available and will serve as the vibrating feeder bowl 10 so long as it is capable of sorting, orienting and feeding the locking bars (or others parts) single-file to the conveyor 20.

The components are transported by the vibratory feed conveyor 20 in a single file and continuous stream. The feed conveyor 20 may be any suitable small parts conveyor although in the presently preferred embodiment is a vibratory conveyor (linear track). The vibration frequencies and hence the feed rates of both the vibrating feeder bowl 10 and vibratory conveyor 20 are adjusted by individual linear amplifiers (shown and described below with regard to FIG. 10).

The sorting assembly 40 includes an ultra-high-speed pneumatic sorting/positioning matrix 60 that singulates, transfers and reorients the components through the various camera-inspection and mechanical-gauge-inspection stations for combined gauge and visual tolerance checking. The embodiment of FIG. 2 is configured for inspection of the locking bar 94 of FIG. 1, and for this purpose sorting/positioning matrix 60 includes a precision length measurement station 62, then a first visual inspection station 65 for tolerance inspection in an X plane, a first mechanical gauge station 61 for thickness and straightness sorting, a coining station 80 for coining failed locking bars, and a second mechanical gauge station 67 for confirming success of the coining station 80.

More specifically, each locking bar is singulated and gated into the sorting/positioning matrix 60 of sorting assembly 40 from the single-file conveyor 20. The locking bar is then pneumatically transferred through three inspection stations, beginning with a length measurement station 62, then to a first visual inspection station 65 beneath camera 30 for optical inspection, and then to a mechanical gauge station 61 for thickness and straightness sorting. The length measurement station 62 comprises any suitable high-precision length measurement sensor, a linear measurement interferometer being preferred. Optical camera imaging is provided by mast-mounted overhead optical inspection cameras 30 in communication with a remote display such as a laptop computer 90. The camera 30 images the locking bar along an X plane for visual tolerance checking relative to a gradient scale displayed on computer 90. The sorting/positioning matrix 60 then ushers the components through a pre-calibrated mechanical gauge station 61 comprising a digital-output micrometer adjusting a fixed-dimension pass-through gate (described below). The locking bar passes through this first mechanical gauge station 61 for thickness and straightness sorting along an X plane. Locking bars that pass the combined visual and machine-gauge inspections are sorted by a collection station 50 into a good parts bin 52.

Defects identified during the combined visual and machine-gauge inspections are fed to a coining station 80 and then to a supplemental mechanical gauge station 63 for automated coining (remanufacture) and re-inspection of the coined parts. If the coined locking bars now pass the supplemental machine-gauge inspection, they are likewise sorted by collection station 50 into the good parts bin 52.

Second-time defects are sorted by collection station 50 left or right, mechanical gauge rejected parts into bin 51, and optical inspection rejected parts into bin 53.

A programmable controller with a touch screen display 70 synchronizes the entire operation, which, even if coining is required, lasts no more than 2.3 seconds. The operator simply empties mechanical gauge rejected parts from bin 51, good parts (including failed-coined- and now-good parts) from bin 52, and optical inspection-rejected parts from bin 53. The system as a whole is capable of tolerance-checking down to 0.00011811", with a repeatability of 0.00005906. The automated inspection, sorting and coining system is adaptable with minimal modification for each of the locking bar, rack, and pin components, although the embodiment illustrated and described herein is adapted for inspection of locking bars. The system is highly configurable depending on production needs, owing largely to the flexibility of the sorting/positioning matrix 60. Both number and sequence of inspections may be changed. For example, a second visual inspection may be needed in a Y-plane, and for this purpose a second visual inspection station may be added for tolerance inspection in a Y plane, and a second mast-mounted overhead optical inspection camera 30 also included. In this case the sorting/positioning matrix 60 rotates each locking bar onto its side at a 90° part rotator, and moves it to the second visual inspection station (under a second camera 30) for visual tolerance checking along the Y plane, again relative to a gradient scale displayed on computer 90.

Figure 3:
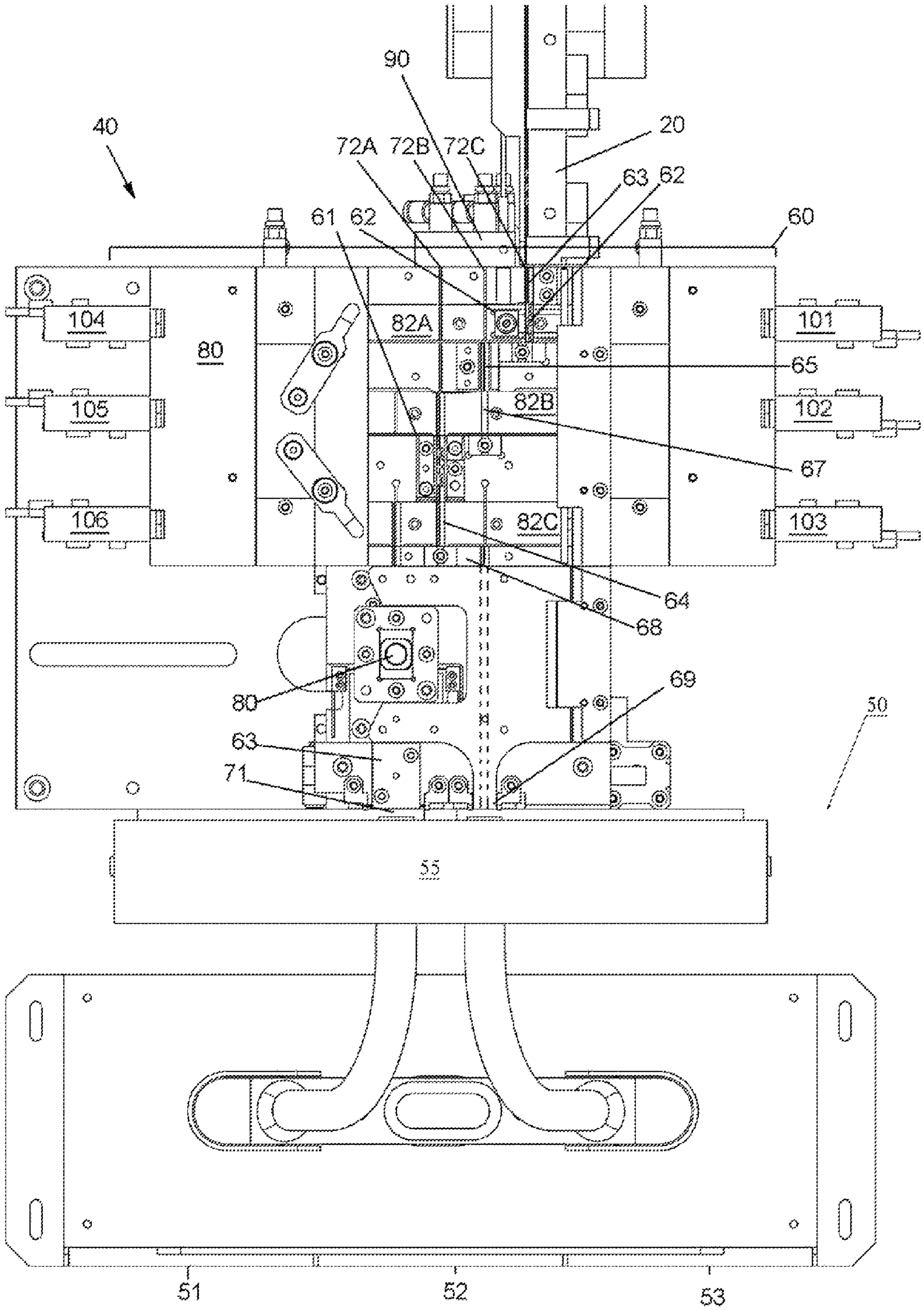
FIG. 3 is an overhead view of the sorting assembly 40, which includes an ultra-high-speed pneumatic sorting/positioning matrix 60.

FIG. 3 is an overhead view of the sorting assembly 40, which includes the ultra-high-speed pneumatic sorting/positioning matrix 60 for singulating, transferring and reorienting the components from conveyor 20 into the various camera inspection and mechanical gauge stations for combined mechanical gauge and optical tolerance checking. Locking bars (or other components) are admitted in a continuous stream, single file in an upright orientation. The components are pneumatically blown into the gate 63, and are gated onward throughout the matrix 60, stopping first at a length measurement station 62, then into a first camera station 65 for optical inspection, and then to a first mechanical gauge station 61 for mechanical inspection, the mechanical and optical inspections being in an X-plane.

Initially the locking bars enter the fixed-position gate 63 with a defined channel to singulate the parts. A pneumatic slide 82A actuated by opposing pneumatic cylinders 101, 104 then gates the individual parts into the matrix 60 under the control of a programmable controller as monitored on the controller's touch screen display 70. The slide 82A slides back and forth pneumatically under control of opposing pneumatic cylinders 101, 104, and parts are gated into slide 82A when it is in the rightmost position (in this position parts shift from the channel in gate 63 into a corresponding channel in the pneumatic slide 82A). The slide 82A itself comprises a length measurement station 62. Presently, length measurement station 62 allows measurement of the length of the locking bars to nanometer accuracy by interferometric optical fibers embedded in the slide 82A channels, thereby providing a nanometer-accuracy linear measurement of each locking bar.

Next, the pneumatic slide 82A moves left to transport the locking bar into a camera optical inspection stations 65. Again, when the pneumatic slide 82A moves left the locking bar is pneumatically blown from the channel in slide 82A into a corresponding channel in optical inspection stations 65, where the component is effectively held stationary within exceedingly close confines for optical inspection using the overhead mast-mounted camera 30 of FIG. 2.

After optical inspection, a second slide 82B shifts left pneumatically under control of opposing pneumatic cylinders 102, 105, and parts are gated into a first mechanical gauge station 61 for mechanical inspection along an X-plane (in this position parts are blown from the channel in optical inspection station 65 into a corresponding channel in the mechanical gauge station 61). Again, the slide 82B moves back to the right to serve as a closed gate. The mechanical gauge station 61 comprises a digital-output micrometer adjusting a fixed-dimension pass-through gate which confirms the thickness of the locking bar.

It should now be apparent that several such slides 82A-C are provided to facilitate movement and gating of the component parts through the various stations, and each is actuated by a pair of opposing pneumatic cylinders 101/104, 102/105 and 103/106 all controlled by the programmable controller 70. The slide positions (left or right) are reported to the programmable controller 70 via sensors mounted on the pneumatic cylinders 101-106.

Depending on the results of the combined inspections, the component is shifted either right or left by pneumatic slide 82C through a singulation station 68 which isolates the component. If it is determined by inspection that the component requires coining, it is transferred left to a coining station 80 which re-manufactures (coins) the parts in real time to resize them. The parts are coined and then sent through a supplemental mechanical gauge 63 to quality-check the coining operation. Coined components that pass the mechanical gauge 63 are gated one-by-one single file through an exit gate 71 at the bottom of the figure, this gating occurring under control of the programmable controller 70. The parts are gated into collection station 50 via a moving shuttle 55 which sorts the parts into good parts bin 52. Coined components that fail the mechanical gauge 63 are shuttled by moving shuttle 55 into mechanical gauge reject bin 51.

Components that do not require coining are gated one-by-one single file through an exit gate 69 at the bottom of the figure, this gating also occurring under control of the programmable controller 70. These components are likewise gated into collection station 50 via a moving shuttle 55 which sorts the parts into the good parts bin 52 or optical inspection rejects bin 53, as appropriate. The programmable controller 70 maintains a synchronous operation by controlling all gating and pneumatics. The inspection performed at each station result in a simple go/nogo determination, the end result of which may be earmarking of parts as good, defective or suitable for coining (remanufacturing).

Figure 4:
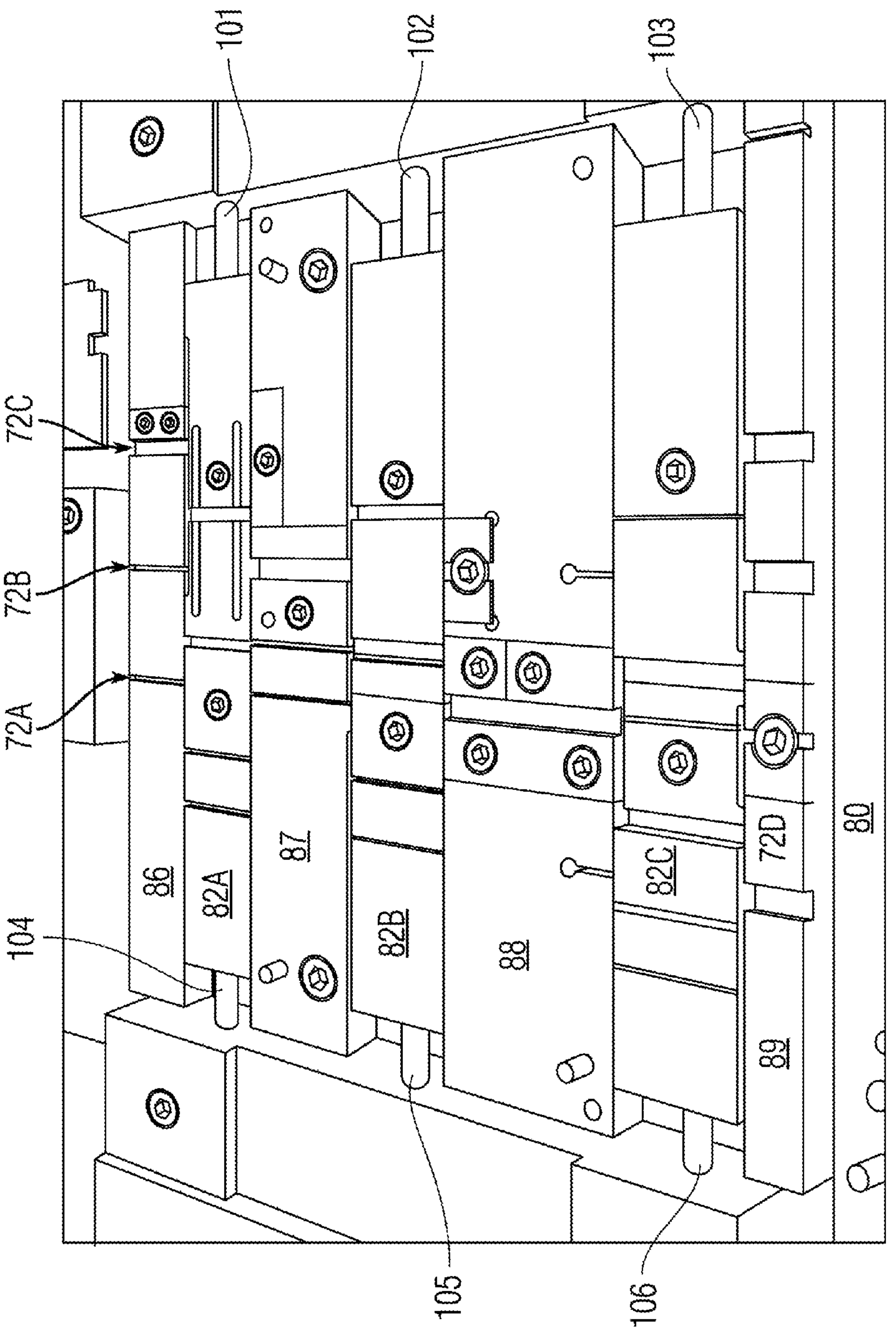
FIG. 4 is a perspective view of the sorting matrix 60 with cover removed to illustrate the mechanics of slides 82A-C

FIG. 4 is a perspective view of the sorting matrix 60 with cover removed to illustrate the mechanics of slides 82A-C, and also showing the pistons of pneumatic cylinders 101/104, 102/105 and 103/106 which facilitate movement of slides 82A-C. The sorting matrix 60 comprises a bed 80 defined by a plurality of fixed-position raised rows 86, 87, 88, 89 (extending horizontally), thereby defining a plurality recessed rows there between. The raised rows 86, 87, 88, 89 are block-inserts screw-attached to bed 80. A plurality of grooves define pneumatic pathways 72A-D running vertically and traversing the raised horizontal rows 86, 87, 88, 89 as shown from end-to-end along the base 80. A plurality of slide inlays 82A-C are slidably mounted in the base 80, each seated within a recessed row. The slide inlays 82A-C likewise each contain grooves corresponding to the pneumatic pathways 72A-D, but the slide inlays 82A-C are pneumatically shifted back and forth by the corresponding pneumatic cylinders 101/104, 102/105 and 103/106 (pistons only shown), which bias the slides 101-103 to shuttle the components between pneumatic pathways 72A-C. Each of the slide inlays 82A-C comprises a rectangular member formed with a component pathway extending there across. When a slide inlay 82A-C is seated in the base 80, the component pathways formed therein correspond to the pneumatic pathways 72A-C formed in the base 80, thereby providing a straight-across component pathway extending end-to-end across the base 80. However, while a component is seated within a slide inlay 82A-C, that slide inlay can be shifted pneumatically left or right to selectively block access of a component, allow entry, and transfer the component into a different one of the pneumatic pathways 72A-C in the next succeeding row 86, 87, 88, 89. Thus, a component part pneumatically moving through one pathway may be offset to another pathway by pneumatic displacement of a slide inlay 82A-C.

Referring back to FIG. 3, an air supply comprises three pneumatic lines coupled into a manifold 90 (at top) for providing air into the corresponding pathways 72A-C for blowing the locking bars through the matric 60. Similarly, twelve pneumatic lines are coupled to the six pneumatic cylinders 101-106 (input and exhaust) for biasing the three slide inlays 82A-C under control of the programmable controller 70 for gating of the component parts through the various stations. This way, the components begin their travel along one pneumatic pathway 72C, and are selectively blocked and/or shifted in transit to other component pathways 72A, 72B, 72D by any of the corresponding slide inlays 82A-C.

All pneumatic lines are controlled by corresponding digital on/off solenoid valves connected to the controller. In the illustrated embodiment there are six pneumatic cylinders 101-106 and three corresponding slide inlays 82A-C, and hence there are twelve solenoid valves and pneumatic lines for moving the three slides 82A-C left and right on each side, in addition to the three pneumatic lines and solenoid valves coupled to manifold 90. Fiber optic sensors are used to detect the part entering and exiting slide inlays 82A-C. This information is communicated to the PLC controller 70 for synchronizing the movements of slide inlays 82A-C. This way, part jams can be detected by the PLC 70 via the fiber optic sensors. The PLC 70 will stop the slide inlay 82A-C movements and the jam will be reported by an error message. The six pneumatic cylinders require twelve air lines (each cylinder takes both input and exhaust air lines). This configuration allows centralized automatic high speed synchronous on/off operation, and pressure control, by the programmable controller 70. The pneumatic cylinders, solenoid valves and pneumatic lines are commercially-available for example from SMC Inc.

Figure 9:
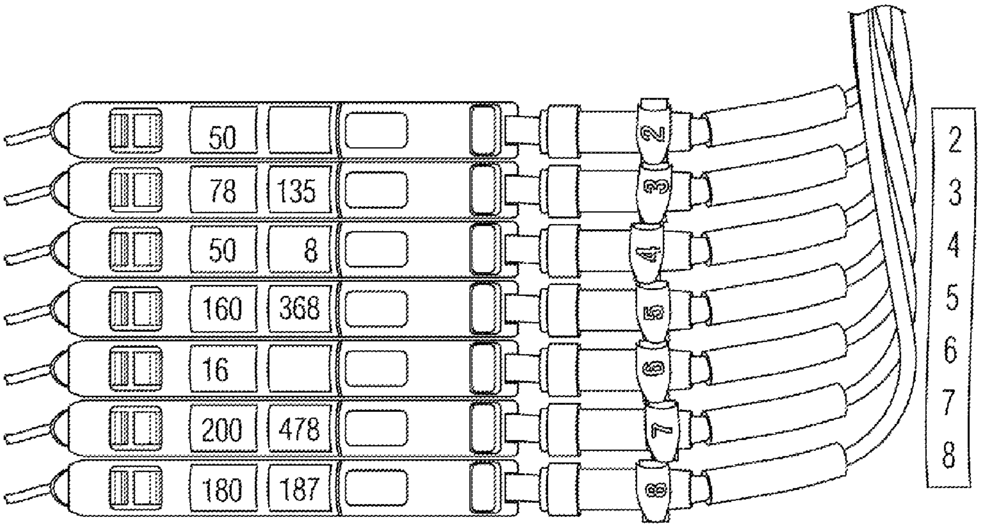
FIG. 9 illustrates the amplifiers used for fiber-optic sensors that sense the position of the locking bar as it is transported from station-to-station by the pneumatic air jets.

As the locking bars travel through the matrix 60 and the system as a whole the individual components positions are tracked by fiber optics. Specifically, FIG. 9 is a front view of amplifiers used for fiber-optic sensors that sense the position of the locking bar as it is transported from station-to-station by the pneumatic air jets. The amplifier gain and triggering thresholds are set during the system set up and calibration. The actual fiber sensors are directed as desired at the various stations to track component progress.

Figure 10:
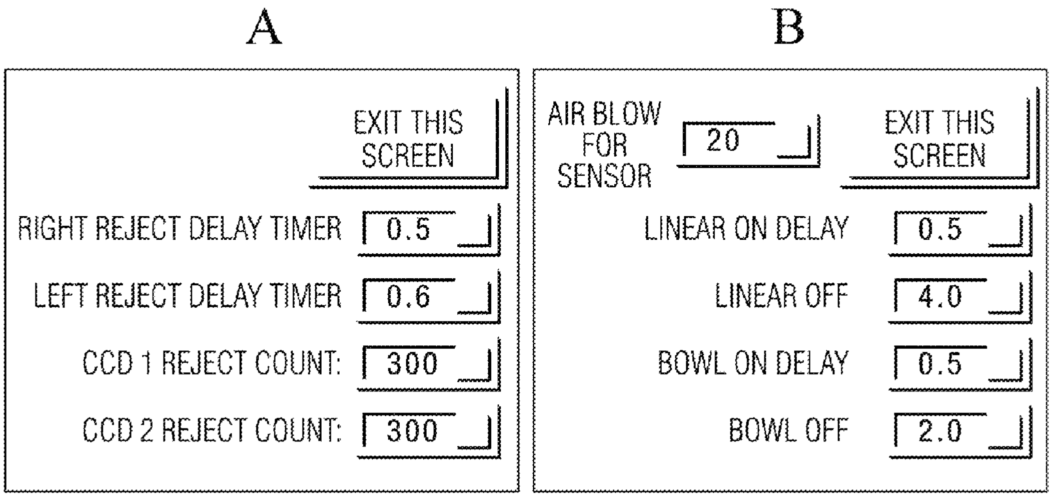
FIG. 10 are photographs of two programmable controller 70 screens showing the set up parameters for the set up and calibration of the locking bar sorter.

FIG. 10 illustrates menus appearing on the touch screen display 70 of the programmable controller. The touch screen display 70 provides a user-interface of various setup screens, the two provided (A & B) illustrating setup of the timing sequence of the process, including air pressure settings, delay settings and maximum reject count.

Figure 11:
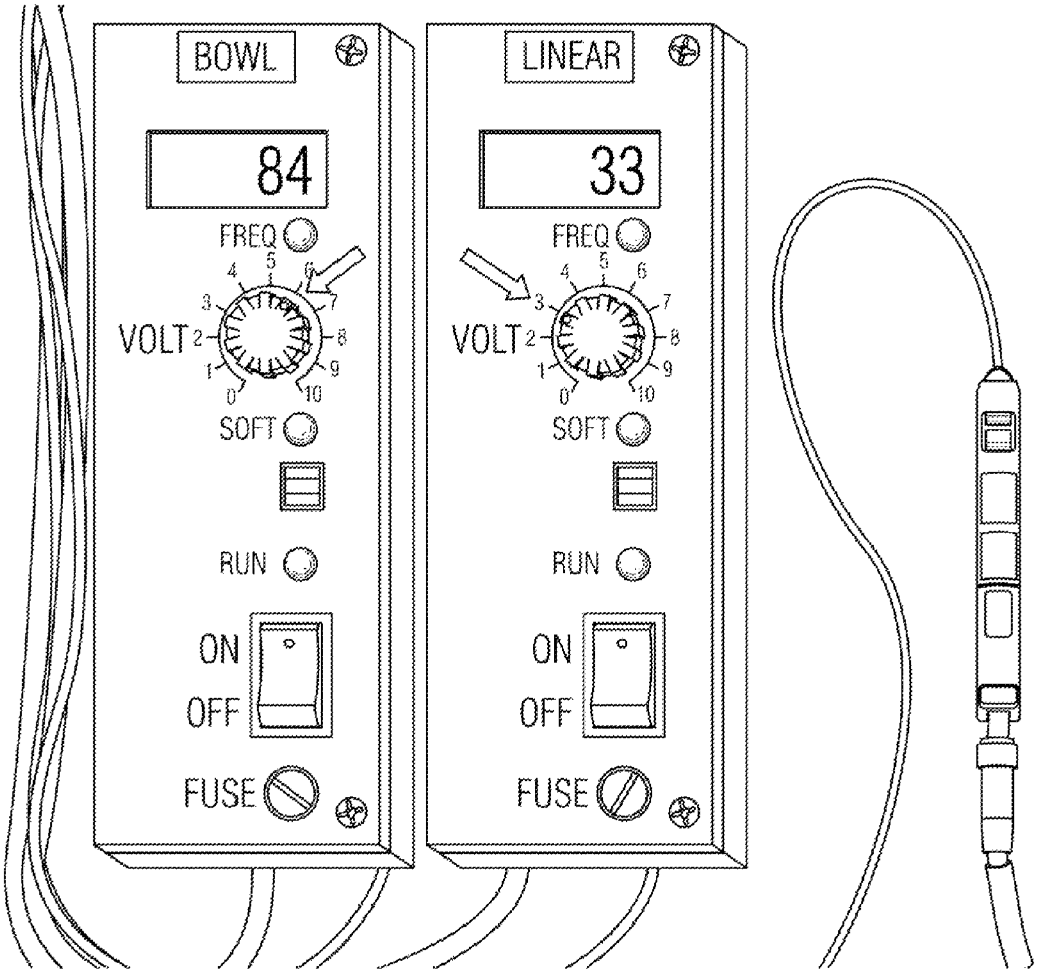
FIG. 11 illustrates the two amplifiers for controlling the feed rates of the feeder bowl and the linear track used for orienting and dispensing the locking bars.

FIG. 11 shows the amplifiers for controlling the vibration frequencies and hence the feed rates of both the vibrating feeder bowl 10 and vibratory conveyor 20.

Figure 12:
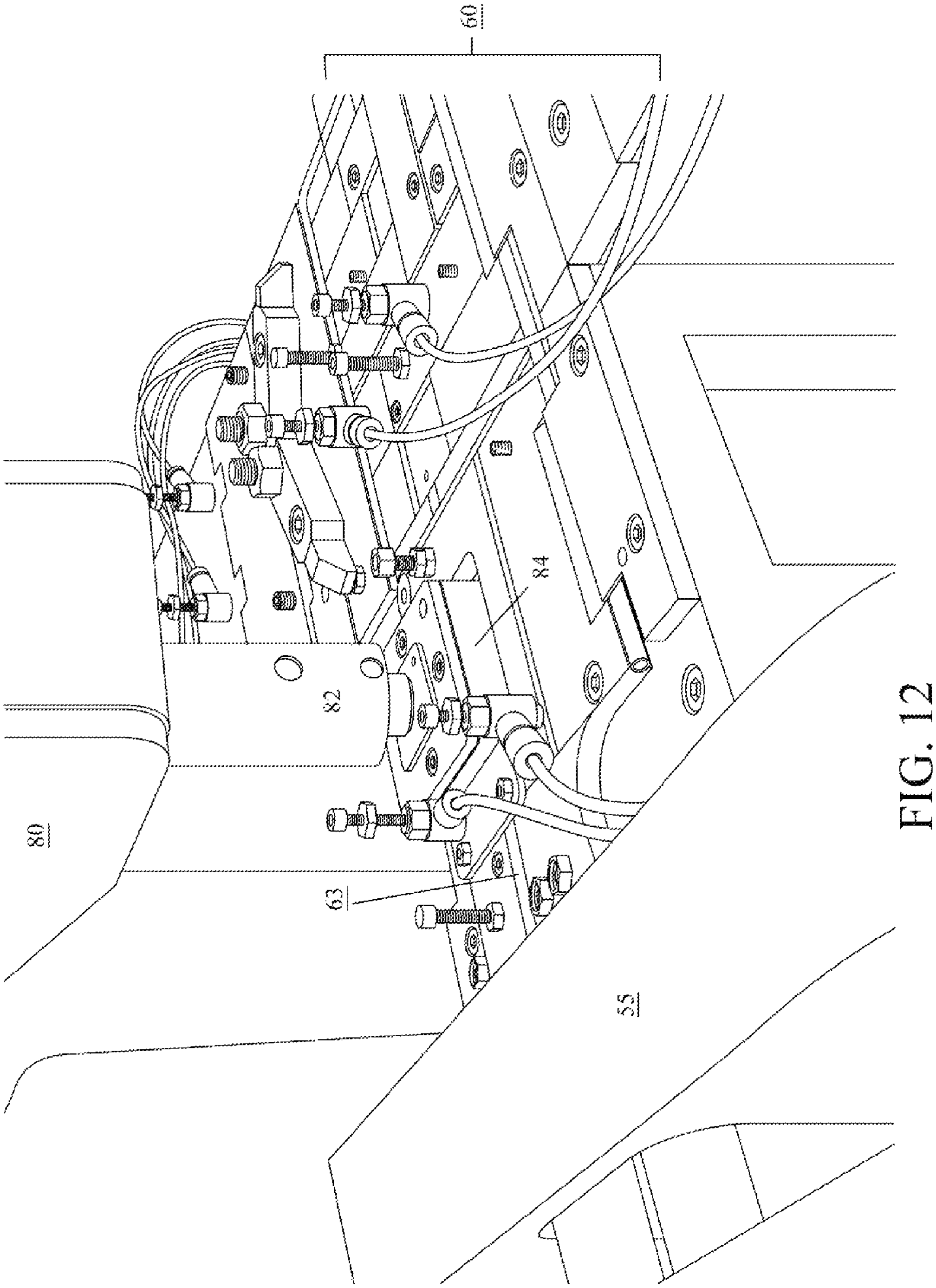
FIG. 12 is a perspective close-up view of the coining station 80.

FIG. 12 illustrates the coining station 80 and supplemental mechanical gauge 63 for coining and re-inspection to straighten bent or oversized parts. Components that failed an inspection (optical or mechanical) are diverted off the pneumatic sorting/positioning matrix 60 and are pneumatically transferred and reoriented into a coining die 84 beneath the coining ram 82 of a hydraulic press. The coining ram 82 imparts a great deal of force to plastically deform the components so they conform to the die 84. The press itself is a commercially-available hydraulically actuated press, a variety of which are readily available. A 50 ton press is acceptable for the present components, and the die 84 may vary depending on the type of component. After each component is coined it is transported to a mechanical gauge station 63 for mechanical inspection. Mechanical gauge station 63 is similar to the above-described micrometer-calibrated mechanical gauge station 61, and likewise comprises a digital-output micrometer adjusting a fixed-dimension pass-through gate which confirms that the coining station 80 was successful. If the component fails again it is sorted into rejected parts bin 51, and if it passes it is sorted into good parts into bin 52.

Referring collectively to FIGS. 3-7, a more detailed explanation of the above-described sorting/positioning matrix 60 is provided. The matrix 60 comprises the cross-hatch pattern of slide inlays 82A-C and pneumatic pathways 72A-C defining fixed-length cells within which the components can be trapped in an exact stationery position. The particular number and placement of the cells and pathways through the pneumatic sorting/positioning matrix 60 may vary as needed, and in the illustrated embodiment one cell defines length measurement station 62, one cell defines camera optical inspection stations 65, and one cell defines mechanical gauge station 61. In each of these stations the component is effectively held stationary within exceedingly close confines, where it can be accurately inspected. A component traverse through the high-speed pneumatic sorting/positioning matrix 60 will now be described with reference to FIGS. 3-7. In summary, the sorting/positioning matrix 60 accomplishes the following steps:

1) orients the locking bars vertically;
2) singulates each locking bar;
3) transports to length measurement station 62 and stops for length measurement;
4) transports to Camera Station 65 and stops for optical inspection;
5) transports to first mechanical gauge station 61 and stops for mechanical inspection;
6) transports rejected locking bars for coining to coining station 80.

After leaving the sorting/positioning matric 60 the locking bars are coined at coining station 80, transported to supplemental mechanical gauge station 63 for follow-up mechanical inspection, and sorted by shuttle 55 into one of three bins: 1) Mechanical Gauge rejected parts into bin 51; 2) coined and now-good parts into bin 52; and 3) Optical Inspection rejected parts into bin 53.

If a second (optional) optical inspection along a Y-plane is desired, after step 5 the locking bar may be rotated 90°, transported to a Camera 2 Station for a Y-plane optical inspection, and then transported to mechanical gauge station 61 for mechanical inspection. This entails the addition of a fourth slide, two additional pneumatic cylinders, four solenoids, and a second overhead camera 30, all of which is readily possible given the reconfigurable nature of the system.

Figure 5:
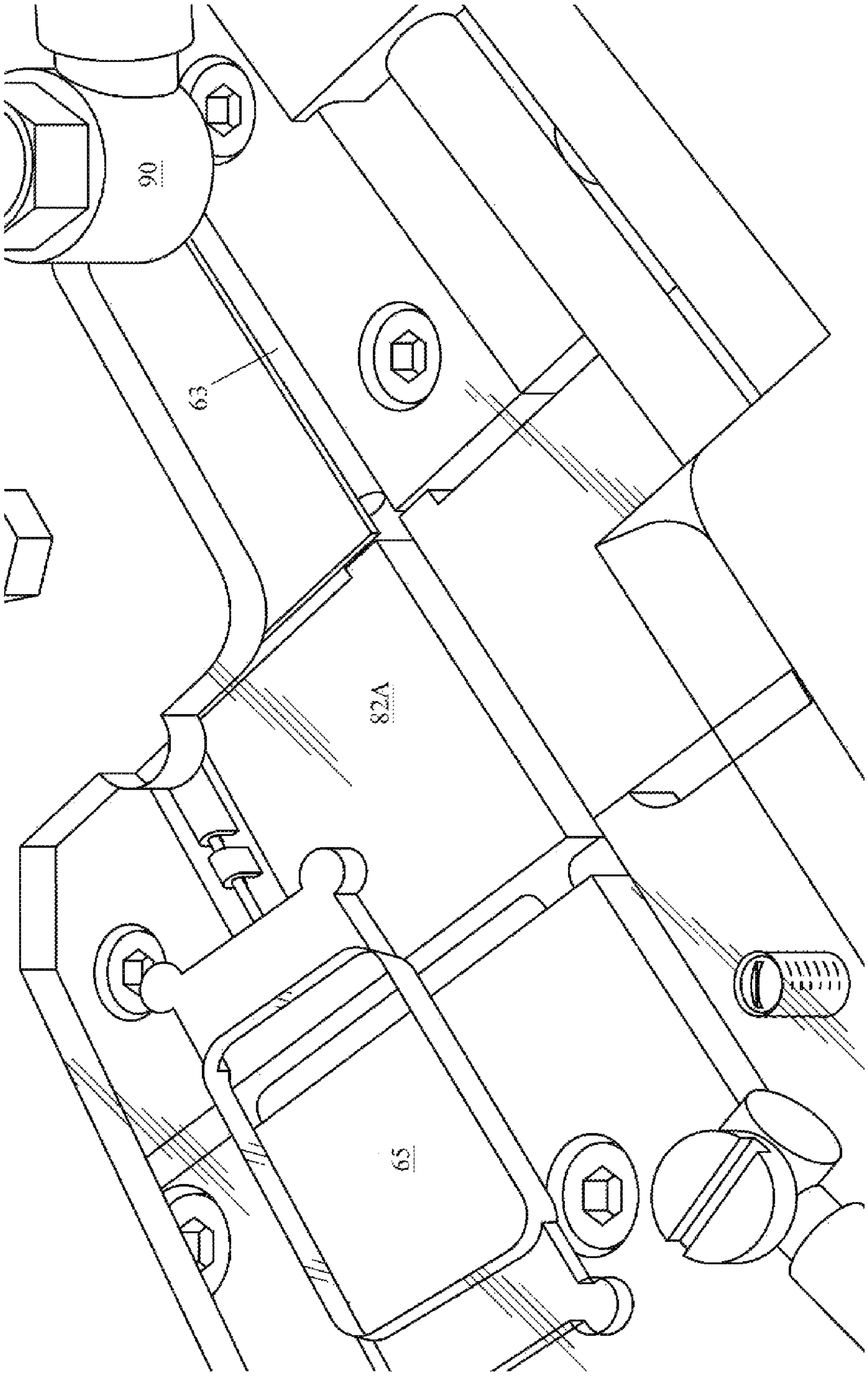
FIGS. 5, 7 and 8 are sequential overhead views illustrating a component traversing the high-speed pneumatic sorting/positioning matrix 60.

At step 1, with reference to FIG. 5, a locking bar is gated into position at gate 63 by air pressure from manifold 90, and is initially stopped by the slide inlay 82A which is displaced leftward. The narrow slot of gate 63 orients the locking bar in a vertical position.

At step 2, the locking bar is singulated within gate 63 (e.g., isolated as a discrete component).

At step 3, slide inlay 82A is displaced right (as shown) and the locking bar enters slide inlay 82A which serves as length measurement station 62. Here it stops for length measurement by a high-precision interferometric length measurement sensor with fiber-optic probe tips embedded in the walls of slide inlay 82A. One skilled in the art should understand that other types of length measurement sensors may suffice for this operation.

Figure 6:
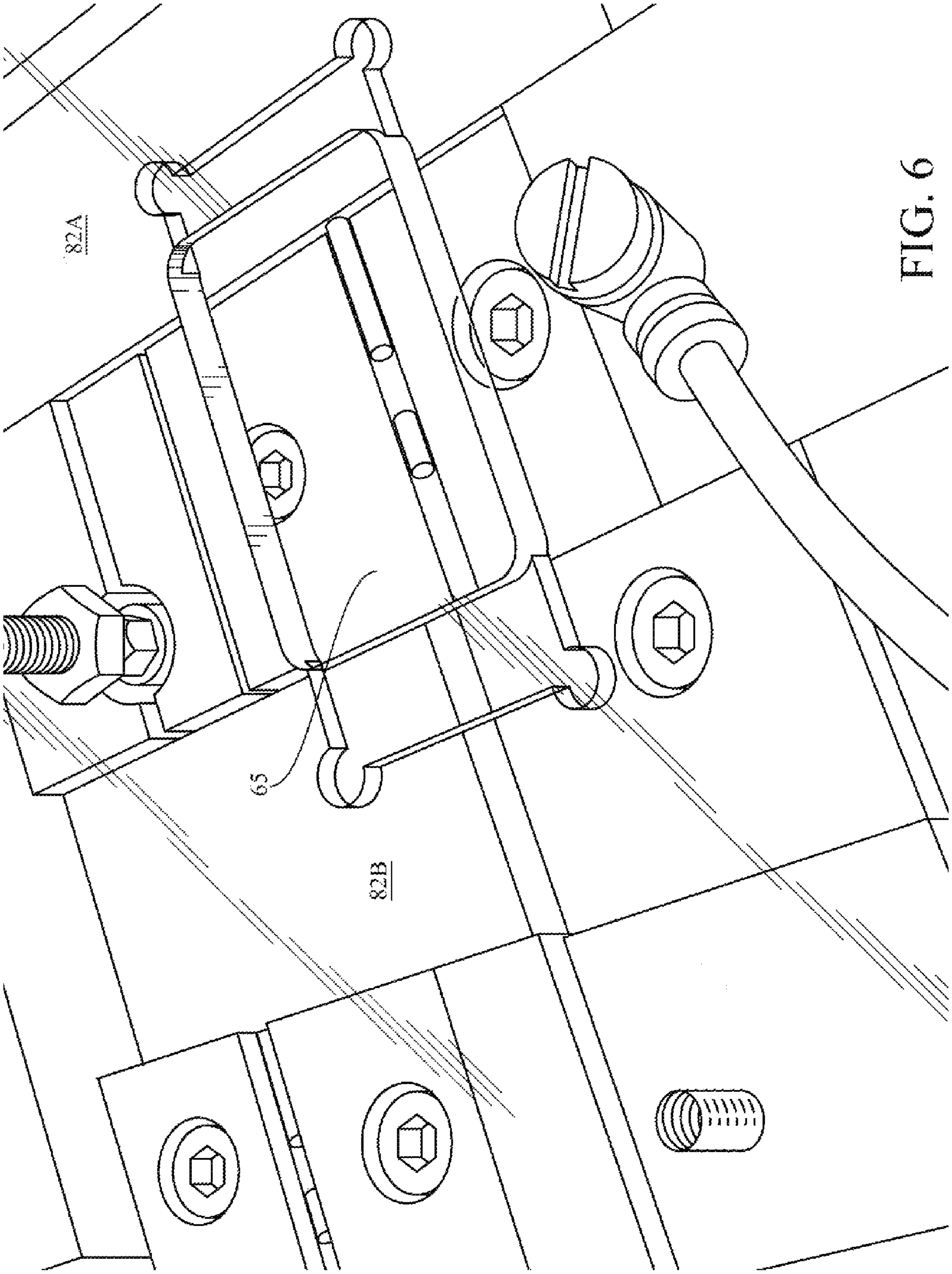
FIG. 6 shows the locking bar images captured by the cameras in the vertical and then after 90° rotation in the horizontal positions.

At step 4 with reference to FIG. 6, under control of programmable controller 70, the slide inlay 82A is urged left thereby aligning the slots with that of the Camera Station 65. Pressurized air from manifold 90 injects the locking bar into Camera Station 65 for optical inspection. Note that the next successive slide inlay 82B is initially in a blocking position, capturing the locking bar at the Camera Station 65. The mast-mounted overhead optical inspection camera 30 zooms in and images the locking bar through the window. In optical inspection station 65 the components are illuminated from the back with red light. A red sharp cut filter 640 nm is attached to the front of the camera 30 to reduce ambient light interference. Note that the camera station 65 is fronted by a plastic window imprinted measuring indicia for optical inspection by camera 30.

Figure 7:
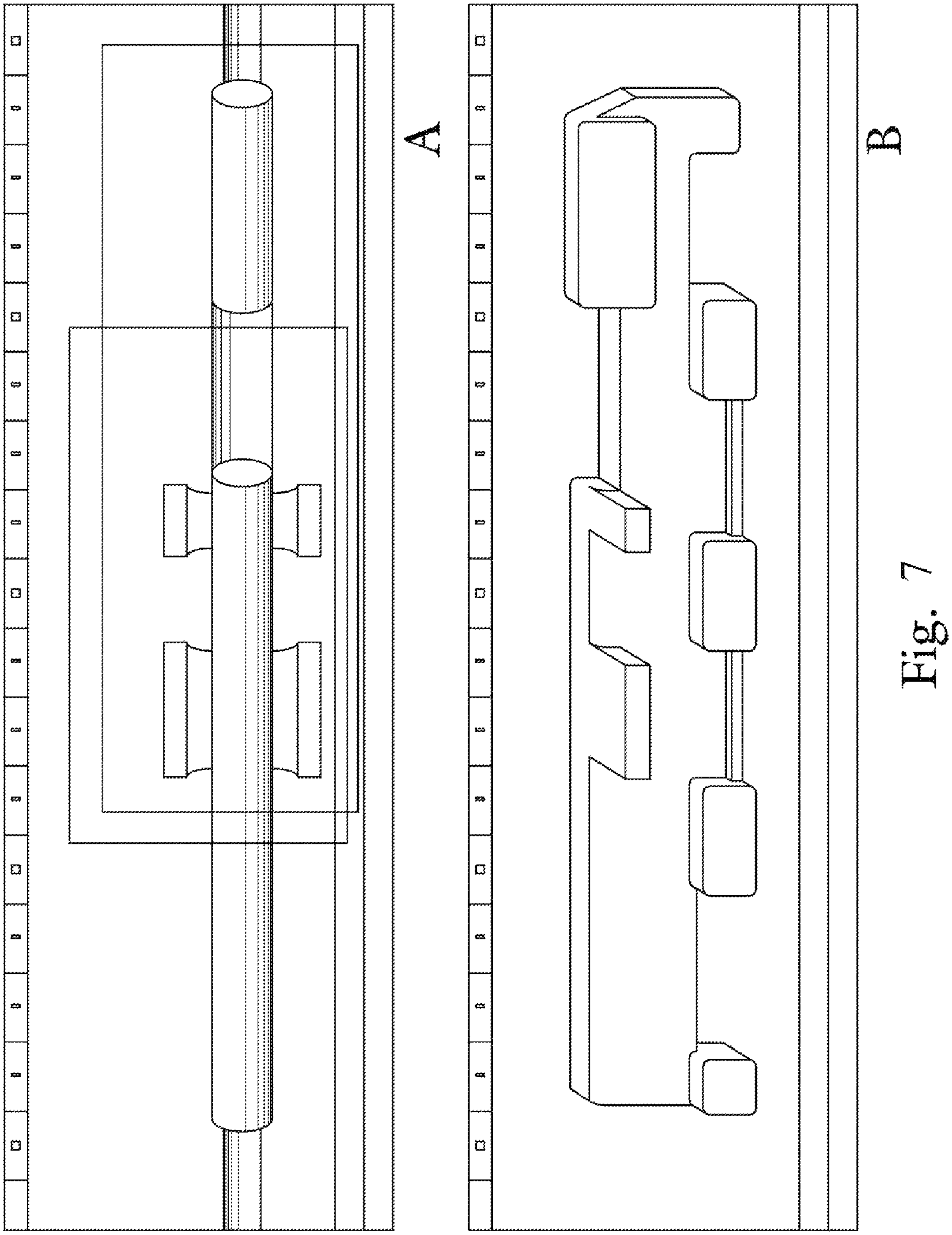

FIG. 7A illustrates the optical inspection image which may be provided to the user. The Camera Station 65 has a resident controller that works in a “hand shake” communication mode with the programmable controller 70 so that images can be viewed on a flat screen monitor such as computer 90. Specifically, the camera 30 images the locking bar along an X plane for visual tolerance checking relative to the gradient scale which is also displayed on computer 90. If a second (optional) optical inspection along a Y-plane is desired, the locking bar would be rotated 90°, transported to a second camera station for a Y-plane optical inspection by another slide (not shown), thereby providing a rotated image at computer 90 as seen at FIG. 7B. Camera 30 is equipped with an on-board controller capable of operating independently from the main controller 70. The camera controller communicates with the main PLC controller 70 via any suitable “hand shake” communication protocol (RS-232 or otherwise). Thus, the camera 30 will send signals to the main PLC controller 70 such as “wait I am checking the image” or “I am done”, “good part or bad part”. The main PLC controller 70 will reply “I got it”, complete the task, and tell the camera(s) 30 to “perform next task”. The controllers of Camera Station 65 may employ software for differentiating good part or bad parts, and so ultimately it may not be necessary to provide an optical inspection image to the user at all. Nevertheless, for present purposes a standalone IBM PC 90 was networked to the camera 30 in order to program the camera parameters, and the optical inspection images of FIG. 7 were displayed on this IBM PC. The images of FIG. 7 serve to illustrate the optical inspections made by the camera station(s) 30. The locking bar is held in a vertical position in Camera Station 65 long enough the Camera Station 65 to take a still image, whereupon the controller or operator completes an accurate software or visual inspection making sure that the locking bar fits within a predetermined footprint of programmed grid lines. Again, software resident on the controller adds the capability to auto-compare the component against pre-existing gridline-footprint data. A variety of commercial software packages exist for this purpose. The software provides full 2D-geometric inspection capabilities along the side-edges of the locking bar. The software automatically tests go/nogo.

Figure 8:
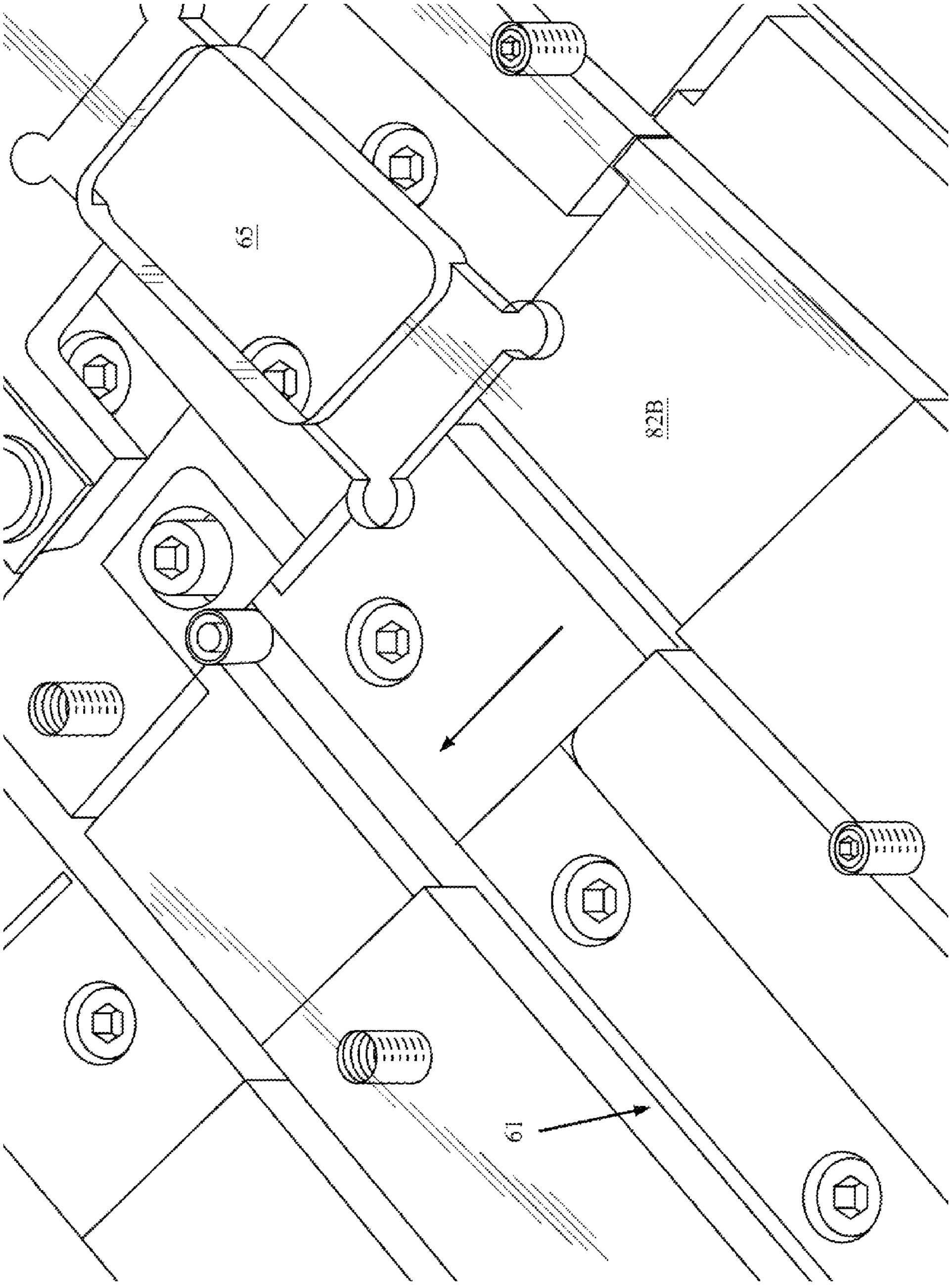

As seen in FIG. 8, at step 5 with a successful first optical inspection complete, slide inlay 82B is displaced first to the right and the locking bar is injected by pressurized air into the slide inlay 82B, and then the slide inlay 82B is shifted to the left (arrow) where it is injected into the first mechanical gauge station 61, for mechanical inspection by micrometer. The mechanical gauge station 61 comprises a digital-output micrometer adjusting a fixed-dimension pass-through gate. While seated in the first mechanical gauge station 61, the width of the locking bar is checked at the pass-through gate, which has a dimension fixed by a digital micrometer. If the locking bar passed the optical inspection station 65 and can pass through the gate 61 the next slide inlay 82C is displaced right and the locking bar is shifted right into a pass track where it is transferred to the good parts bin 52. Once the gate 61 dimension is set by the micrometer to a part-specification, the part either passes through or not, indicating a pass or fail component. If a part is bent or if it is over-thickness, the gate 61 gauge plates are temporarily opened to let the part through. However, the gauge plate 61 moves precisely back to the original position after the oversized part passes. The position of the moving gauge plate 61 is monitored by a high precision sensor and controlled by the programmable controller 70 to 0.0001". The same micrometer/gate configuration is used in the supplemental mechanical gauge station 63 following the coining station 80.

At step 6, if the locking bar fails any optical or mechanical inspection, the next slide inlay 82C is displaced left and the locking bar is shifted left into a reject track where it is transferred to reject bin 51 (or optionally coining bin 53). As described above with reference to FIG. 12, the coining station 80 coins the failed part to straighten bent or oversized parts (via coining die 84 beneath the coining ram 82 of a hydraulic press), and supplemental mechanical gauge 63 re-inspects the coined part.

All the inspected and optionally coined components accumulate at collection station 50 in the three bins: 1) rejects in bin 51; 2) good parts in bin 52; and 3) optical inspection rejects into bin 53. The parts are gated out of the sorting matric 60 or supplemental mechanical inspection station 63 into collection station 50 via a moving shuttle 55 which collects the parts and moves them into the appropriate bin. Good parts are shuttled to bin 52, parts that fail optical inspection and are not coined are rejected into bin 53, and coined components that fail the mechanical gauge 63 are shuttled by moving shuttle 55 into mechanical gauge reject bin 51. The entire process is controlled by the programmable controller in accordance with the user-settings entered by menus appearing on the touch screen display 70 (FIG. 10), including the timing sequence of the process, air pressure settings, delay settings and maximum reject count.

It should now be apparent that the above-described visual inspection station(s), mechanical inspection station(s), coining station(s), and component sorters and component dispensers provide ultra-high-speed pneumatic sorting and reorientation of the components into the various camera inspection and gauge stations for combined gauge and visual tolerance checking. Although the Locking Bar System Configuration described above includes a visual inspection station and mechanical gauge for thickness and straightness sorting in the X plane, one skilled in the art should readily understand that various related configurations are possible depending on the particular component part to be inspected and the inspection goals of the operator. Specifically, it is envisioned that the following combinations will serve the corresponding component parts:

1. Rack-Testing Configurations a. Visual Inspection Station plus Mechanical Gauge for thickness and straightness sorting;

b. Mechanical Gauge with Coining for resizing parts, and another Mechanical Gauge to sort resized parts;

c. Visual Inspection Station with Mechanical Gauge and Coining for Resizing Parts and another Mechanical Gauge to sort resized parts;

2. Pin-Testing Configurations a. Feeder Bowl to separate unwanted welded pins (Caused by MIM Sintering Process) from single pins;

b. Welded Pin Separator and Visual Inspection Station

3. Locking Bar-Testing Configurations a. Visual Inspection Station with Mechanical Gauge for thickness and straightness sorting in the X plane, 90° Part Rotator and Visual Inspection Station with Mechanical Gauge for thickness and straightens sorting in the Y plane;

b. Mechanical Gauge with Coining for Resizing Parts, followed by Mechanical Gauge to sort resized parts;

c. Visual Inspection Station with Mechanical Gauge and Coining for resizing parts, followed by Mechanical Gauge to sort resized parts.

In all the foregoing exemplary configurations it is possible to electronically enable or disable all or some of the stations. For example, for the Locking Bar System, Configuration (a), it is possible to turn OFF the visual inspection station and leave ON the Mechanical Gauge, or vice versa.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A pneumatic sorting matrix for transporting and positioning small component parts for inspection, comprising:

a base having a surface defined by a plurality of raised rows and at least one recessed row between said raised rows, and at least two parallel grooves traversing each of said raised rows and partially defining a first pneumatic part pathway and a second pneumatic part pathway;

a first slide inlay slidably mounted in said at least one recessed row, said first slide inlay being defined by a groove traversing said first slide inlay parallel to the grooves of said raised rows, and fully defining said first pneumatic part pathway when said first slide inlay is in a first position, and fully defining said second pneumatic part pathway when said first slide inlay is in a second position;

an air supply in communication with said first pneumatic part pathway and said second pneumatic part pathway for blowing a component part there along;

a first actuator for selectively shifting said slide inlay between said first and second positions to shuttle a component part between said first and second pneumatic part pathways; and a programmable logic controller in communication with said pneumatic actuator and said air supply for controlling traverse of said blown component part down said first pneumatic part pathway, said second pneumatic part pathway, or a combination of said first and second pneumatic part pathways.

2. The pneumatic sorting matrix according to claim 1, further comprising a control gate positioned in one of the grooves in a raised row of said base and in communication with said programmable logic controller for interrupting traverse of said component part and positioning said part for inspection.

3. The pneumatic sorting matrix according to claim 1, wherein said base further comprises at least three raised rows with at least two recessed rows there between, said first slide inlay being slidably mounted in one of said recessed rows and a second slide inlay is slidably mounted in another of said recessed rows.

4. The pneumatic sorting matrix according to claim 3, further comprising a second pneumatic actuator for selectively shifting said second slide inlay between a first and second position to shuttle a component part.

5. An automated system for inspection of precision components, comprising:

a pneumatic sorting matrix for transporting and positioning small component parts for inspection, pneumatic sorting matrix further comprising, a base having a surface defined by a plurality of raised rows and at least one recessed row between said raised rows, and at least two parallel grooves traversing each of said raised rows and partially defining a first pneumatic part pathway and a second pneumatic part pathway, a first slide inlay slidably mounted in said at least one recessed row, said first slide inlay being defined by a parallel groove traversing said first slide inlay and fully defining said first pneumatic part pathway when said first slide inlay is in a first position, and fully defining said second pneumatic part pathway when said first slide inlay is in a second position, and at least one inspection station positioned along said first component part pathway for maintaining said part stationery for inspection;

a first air supply in communication with said first pneumatic part pathway for blowing a component part therealong;

a second air supply in communication with said second pneumatic part pathway for blowing a component part therealong;

a first pneumatic actuator for selectively shifting said slide inlay between said first and second positions to shuttle a component part between said first and second pneumatic part pathways;

a programmable logic controller in communication with said pneumatic actuator and said first and second air supplies for controlling traverse of said blown component part down said first pneumatic part pathway, said second pneumatic part pathway, or a combination of said first and second pneumatic part pathways.

6. The automated system for inspection of precision components according to claim 5, further comprising a first camera for imaging said component part when stationery at at a first inspection station.

7. The automated system for inspection of precision components according to claim 6, wherein said first camera is mounted on a boom overhead said first inspection station.

8. The automated system for inspection of precision components according to claim 6, further comprising a second camera for imaging said component part when stationery at a second inspection station.

9. The automated system for inspection of precision components according to claim 5, further comprising a micrometer-controlled pass-through gate for measuring said component part at said at least one inspection station.

10. The automated system for inspection of precision components according to claim 9, wherein said micrometer-controlled pass-through gate comprises a digital micrometer for calibrating pass-through dimensions of said pass-through gate in said first pneumatic pathway.

11. The automated system for inspection of precision components according to claim 5, further comprising a coining press and die for coining components that fails inspection.

12. The automated system for inspection of precision components according to claim 5, wherein said component part may be any one of a rack, pin and locking bar of a rekeyable lock cylinder.

13. A high-speed pneumatic sorting matrix for moving individual component parts to a plurality of inspection stations, said sorting matrix comprising a base having a plurality of raised rows defining at least one recessed row between said raised rows, and a plurality of parallel channels traversing each of said raised rows, a slide inlay movably mounted in said at least one recessed row, and an actuator for controlled shifting of said slide inlay, whereby a component part pneumatically blown through one channel in one raised row may be offset to another channel in another raised row by actuator displacement of a slide inlay.

14. A method for inspecting component parts using a pneumatic sorting matrix comprising a base having a plurality of pneumatic slides mounted therein, and a plurality of pneumatic channels defined through said base and slides for carrying said component parts, comprising the steps of:

pneumatically blowing a component part along a first pneumatic channel into a first inspection station;

inspecting said component part;

shifting one of said plurality of pneumatic slides to displace said component part to a second pneumatic channel; and pneumatically blowing said component into said second pneumatic channel.

15. A method for selectively transporting individual component parts to a plurality of inspection stations using a pneumatic sorting matrix comprising a base having a plurality of raised rows defining at least one recessed row between said raised rows, and a plurality of parallel channels traversing each of said raised rows, a slide inlay movably mounted in said at least one recessed row, and an actuator for controlled shifting of said slide inlay, comprising the steps of:

blowing a component part pneumatically into a first channel in one raised row;

controlling said actuator to shift said slide inlay to a first position;

blowing said component part pneumatically into said slide inlay while in said first position;

controlling said actuator to shift said slide inlay to a second position;

blowing said component part pneumatically into a second offset channel in another raised row while said slide inlay is in said second position.

* * * * *